United States Patent [19]

Brüning et al.

[11] Patent Number: 4,499,191
[45] Date of Patent: Feb. 12, 1985

[54] METHOD AND APPARATUS FOR THE DECOMPOSITION OF SPECIMENS OF SOLID ORGANIC SUBSTANCES

[75] Inventors: Rolf Brüning, Bruchköbel; Jürgen Roth, Maintal, both of Fed. Rep. of Germany

[73] Assignee: Heraeus Quarzschmelze GmbH, Hanau, Fed. Rep. of Germany

[21] Appl. No.: 375,201

[22] Filed: May 5, 1982

[30] Foreign Application Priority Data

May 13, 1981 [DE] Fed. Rep. of Germany ....... 3118876

[51] Int. Cl.$^3$ ............................................ G01N 31/12
[52] U.S. Cl. .................................. 436/160; 110/263; 422/78
[58] Field of Search ...................... 436/160, 155, 174; 110/263-265; 422/68, 78

[56] References Cited

U.S. PATENT DOCUMENTS

| | | | |
|---|---|---|---|
| 3,116,979 | 1/1964 | Kapff | 436/160 |
| 3,298,785 | 1/1967 | Reul | 422/68 |
| 4,154,585 | 5/1979 | Melcher et al. | 110/263 |

Primary Examiner—Hiram H. Bernstein
Attorney, Agent, or Firm—Frishauf, Holtz, Goodman & Woodward

[57] ABSTRACT

Specimens of solid organic substances are decomposed by grinding the specimen to powder having particles of a size smaller than 75 microns, and then compressing the powder specimen. The compressed powder specimen is abraded by means of a scraper, and the abraded material metered out in predetermined amounts for incineration in an injector burner suitable for solids. In this manner, large quantities of specimen material which might contain elements that attack quartz glass can be incinerated without causing damage to the quartz glass burner. The apparatus for decomposing specimens of solid organic substances includes an injector burner that communicates with a powder processing and proportioning device through a flexible tube. The powder processing and proportioning device includes a specimen container for compressed powder, supported by a rotatable fixture to rotate the specimen container. A plug provided in the specimen container, but having radial clearance with respect to the container walls is held by a vertically movable fixture that furnishes movement to the plug along the axis of the specimen container. The scraper for abrading the powder specimen is attached to the plug and is thus movable toward the powder specimen while the container is being rotated. Abraded powder is drawn through the flexible tube to the burner.

10 Claims, 1 Drawing Figure

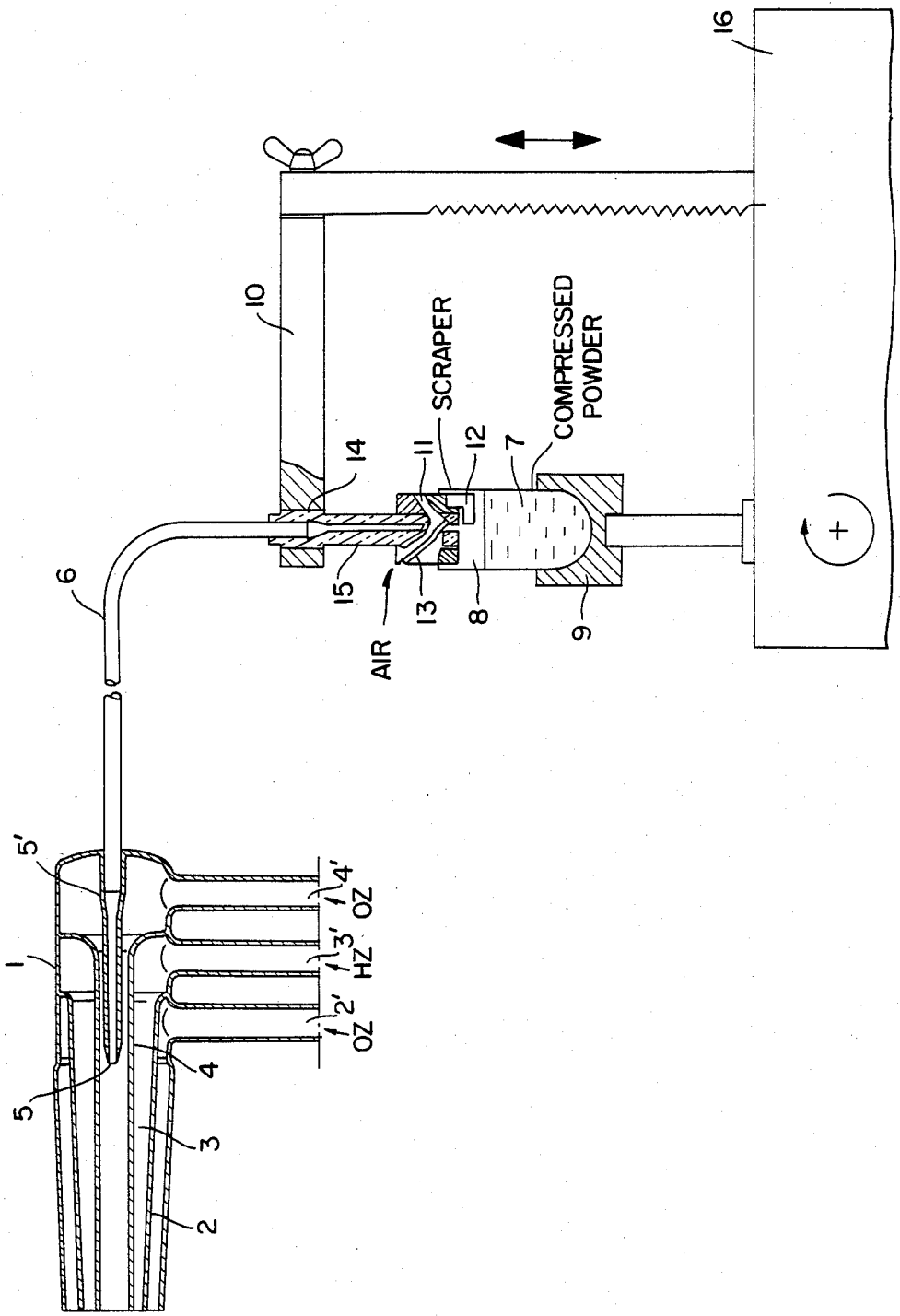

METHOD AND APPARATUS FOR THE DECOMPOSITION OF SPECIMENS OF SOLID ORGANIC SUBSTANCES

This invention relates to the decomposition of specimens of solid organic substances, and more particularly to a method and apparatus for such decomposition using an injection type burner composed of quartz glass.

BACKGROUND AND PRIOR ART

It is known that a determination of the sulfur, halogen or boron content of organic substances can be accomplished by utilizing an injector type burner as described in U.S. Pat. No. 3,298,785. The injector burner is fueled by hydrogen and oxygen gas to disintegrate the organic substances of interest in an oxidizing atmosphere, in a closed water-cooled combustion chamber. The products of combustion are collected in an aqueous solution for subsequent analytical determination. (Wickbold Method, Angewandte Chemie (Applied Chemistry) Vol. 64, 1952, No. 5, pages 133–135. Publishing House Chemie).

To decompose solid substances according to this method, special burners made of quartz glass are used with a gasification chamber positioned in front of the flame. A specimen of the solid organic substance is subjected, either directly or in a laboratory boat, to a coking process whereby heat is applied from the outside while the substance is exposed to nitrogen. The flow of nitrogen conveys the volatile products of the coking process into the flames of the burner. Oxygen is then added after completion of the coking process so that the end residue is completely oxidized in a pure oxygen stream. (Heraeus Quarzschmelze—Prospect Q.—E 1/111.1, 1976) (pamphlet using quartz for fusing processes).

This known method is suitable for organic substances that do not contain any of the elements, e.g. alkali metals, alkaline earth metals, boron and phosphorus, which attack the quartz glass of the burner. To avoid damage to the quartz glass, the organic substance, including the mentioned elements, are brought into solution, if possible, and thereafter burnt up in an injector burner suitable for liquids. In this manner the elements which can cause damage to the quartz do not come in contact with it so that the undesirable recrystallization of the quartz glass is avoided. When specimens of solid biological substances are decomposed and contain the aforementioned damaging elements, the gasification chamber of the burner, which is usually comprised of quartz glass, is subjected to a damaging recrystallization or fusing action. Thus deterioration of the burner can occur after only a few decomposition determinations.

The external heat supply for the coking process is generally furnished by means of a gas burner guided manually so that effectuation of the incineration process depends to a large extent upon the skill of the operating personnel. The specimen quantity is usually limited to a weight of from 0.5 to 2 grams. Due to the reaction of the products of combustion with the hot quartz glass of the gasification chamber a considerable amount of the specimen substance cannot be utilized for its intended purpose.

THE INVENTION

It is an object of the present invention to provide a method and apparatus for decomposing a solid organic substance by feeding the substance in solid form directly into the combustible gas-oxygen flame of a burner without pre-incineration. Thus the advantages of an injector burner for liquids can also be had in the combustion of solid substances.

According to the invention a powder sample with particles having a size of under 75 microns is removed from the specimen of the solid material and placed into a specimen container where it is compressed. Thereafter, solid material is continuously abraded from the free surface of the compressed powder by a scraper, and drawn into the center tube of the burner by means of a flexible suction hose. A commercially available laboratory crusher, such as a ball mill, can be used to produce the powder, preferably with a particle size of less than 60 microns. Advantageously the specimen container is continuously rotated, with the scraper remaining stationary.

In a preferred apparatus for implementing the process of the invention the specimen container holding the solid organic substance is arranged on a rotating fixture and has a plug, provided with a center bore, projecting into the specimen container. The center bore of the plug communicates with a center tube of the burner by means of a flexible tube. A small clearance is provided between the plug and the wall of the container to permit rotation of the container with respect to the plug.

A scraper is attached to the bottom surface of the plug extending toward the compressed power in the specimen container. The plug is secured by a holding fixture which is movable in the axial direction of the specimen container to provide relative linear movement between the scraper and the compressed powder. Therefore during rotation of the specimen container the scraper can be constantly advanced in the axial direction toward the compressed powder. Moist specimens of solid matter can be subjected to freeze-drying before pulverization.

According to the invention the plug includes a channel with parallel walls extending obliquely on the plug periphery starting at the upper face of the plug and ending at the lower face thereof at the location of the scraper. The center tube of the burner is in the form of a capillary and includes an orifice disposed rearwardly of the burner orifice. Delivery of the scraped-off powder to the burner is effected by means of a directed air stream flowing from the plug, through the flexible tube, to the center tube of the burner.

An advantage of the method and apparatus in the avoidance of damage to the quartz glass components and the ability to decompose solid organic substances which contain elements that react with hot quartz glass as well as those specimens, such as sugar, which swell up considerably during the coking process. A further advantage is that any selected quantity of the specimen can be used since there is continuous combustion of the powder. The processing of large quantities of powder merely requires longer combustion times. However the disclosed apparatus can be made to any feasible size to increase the output and is especially effective for determinations relating to trace analysis.

Furthermore considerably less time is necessary for decomposing a specimen of a solid organic substance than in known decomposition apparatus. For example, flow rates of from 0.2 grams to 5 grams per minute can be realized for the combustion of tobacco or cereal flour. Operation of the apparatus is relatively simple and provides results that are less dependent upon the skill of operating personnel than for previously known decomposition apparatus. All the incinerated products of the burnt specimen reach the analytical solution in finely dispersed form. Therefore it is not necessary to extract such products separately from the coking chamber. Consequently when the determination of metallic element is conducted, the carbonate-containing ash can be dissolved immediately in the acidic solution in the receiving vessel, thereby simplifying the determination of trace elements in specimens of solid biological substances.

The drawing illustrates, in schematic form, the apparatus of the invention by which the method thereof can be practiced.

A burner 1 includes annular jets 2, 3 and 4 that communicate with respective connections 2', 3' and 4'. The connections 2' and 4' deliver oxygen whereas the connection 3' delivers hydrogen. The burner 1 also includes a powder delivery center jet 5 having an enlarged end portion 5'. A flexible tube 6 is connected at one end to the burner 1 at the enlarged end portion 5'. An opposite end of the flexible tube 6 is connected to a quartz glass capillary 15 of the hereinafter described powder processing and proportioning device.

The quartz glass capillary 15 is mounted in a holding fixture 10 and has an enlarged bore 14 that receives the flexible tube 6. The other end of quartz glass capillary 15 is fitted into the center bore of a plug 11. A slightly compressed powder specimen 7 is disposed in a specimen container 8 supported by a fixture 9 which rotates about a vertical axis of the specimen container. The height of the holding fixture 10 can be adjusted with respect to a base 16 along the axis of the specimen container.

The plug 11 has a radial clearance in the specimen container 8 of slightly less than 0.2 mm. A scraper 12 located on the lower side of the plug 11 is arranged in a radial or worm-like configuration. A spiral channel 13 starts at an upper peripheral edge of the plug 11 and ends in the center of the plug.

OPERATION

The rotation of the specimen container 8 and an automatic lowering of the holding fixture 10 at a slow adjustable vertical speed are controlled by individually adjustable electromotive drives (not shown) in the base 16 to ensure that the height adjusting and rotation parameters can be optimally set according to the physical characteristics of the specimen 7. A thin layer of powder is uniformly abraded from the surface of the rotating compressed specimen 7 of the solid substance by means of the slowly descending scraper 12. The abraded powder is transported through the quartz glass capillary 15 and the flexible tube 6 to the quartz glass burner 1 by virtue of a vacuum condition in the burner 1 and an air stream movement caused by the tangential flow of the inlet air in the channel 13. Due to the small cross-section of the capillary 15 the abraded powder particles attain a relatively high velocity thereby avoiding the possibility of clogging the capillary 15 through accumulation of powder. Once the powder particles reach the considerably larger cross-section of the center tube 5 their particle velocity is reduced, and after emerging from the center tube 5 is considerably diminished.

The particles thus become thoroughly interspersed with oxygen for complete incineration due to sufficient retention time in the flame of the burner 1. Depending upon the material of the specimen and the supply of powder to the burner 1, the speed of combustion of specimen material can be regulated by means of the vertical advance of the holding fixture 10.

A burner unit 1, for example of the type described in the prospectus Q-E 1/111.1, 1976, is used, coupled through a tube 6 of 3 mm inner diameter to the suction apparatus. The specimen 7 was formed as a compressed cake of tobacco powder, which formed a dense mass of about 1 g/ml specific gravity. The surface scraper 12 of stainless steel was moved over the surface thereof, thus generating a fine dust within the specimen container 8, which was introduced into the burner through an orifice 5 of 3 mm inner diameter.

We claim:

1. A method for the decomposition of specimens of solid organic substances in an injector burner (1) consisting of a plurality of annularly interspaced concentric tube (2,3,4 and 5), wherein the substance to be incinerated is introduced into the center tube (5), said method comprising, forming a powdered specimen (7) with a particle size of less than 75 microns from the solid organic substance, placing the powdered specimen (7) into a specimen container (8), compressing the specimen (7) and continuously abrading the specimen (7) to yield solid material in the form of fine dust from the surface of the specimen (7), the abraded material being continuously drawn into the burner (1) through a flexible tube (6) joining the specimen container (8) and the center tube (5) of the burner (1).

2. The method of claim 1 wherein the powder abrading step is accomplished with a scraper (12) held stationary while the specimen container (8) is continuously rotated, and a relative motion in the axial direction of the specimen container (8) is maintained between the scraper (12) and the specimen (7) to cause the scraper (12) to engage and abrade the compressed powder specimen (7).

3. The method of claim 2 wherein the scraper (12) is continuously advanced in the axial direction of the container (8) toward the specimen (7).

4. The method according to any of the claims 1, 2 or 3 wherein the abraded material is delivered in the form of fine dust to the injector burner (1) through the flexible tube (6) by a directed air stream.

5. The method of claim 4 wherein the specimen of solid material is subjected to freeze-drying before abrading.

6. In an apparatus for decomposing specimens of solid organic material including an injector burner (1) having a plurality of annularly interspaced concentric tubes (2, 3 and 4) connected to a combustible gas supply, such as hydrogen and oxygen, and a center tube (5) which is connected through a tube (6) with a specimen container (8) having solid organic material (7), the improvement comprising, a rotating fixture (9) supporting the specimen container (8) for rotation about a vertical axis of the specimen container (8), a plug (11) for the specimen container (8), said plug (11) having a centerbore, a scraper (12) attached to the plug (11) and extending toward the bottom of the specimen container (8), the plug (11) having a predetermined clearance from the wall of the specimen container (8), and a quartz glass capillary (15) having one end in the centerbore of the plug (11), the tube (6) being flexible and connecting the opposite end of the quartz glass capillary (15) to the center tube (5) of the burner (1), and a holding fixture (10) movable in the direction of the axis of the specimen container and arranged to hold the quartz glass capillary (15) for movement of said capillary (15) and said plug (11) in the direction of the axis of the specimen container (8).

7. The apparatus of claim 6 wherein the burner (1) has a mouth and the center tube (5) of the burner (1) is formed in the shape of a capillary having a mouth (5') disposed rearwardly with respect to the mouth of the burner (1).

8. The apparatus of claim 6 wherein the plug (11) includes an upper surface and a lower surface, and a channel (13) extending obliquely along the periphery of the plug (11) and ending at the lower surface of the plug (11).

9. The apparatus of claim 8 wherein the channel (13) is shaped as a fluted slot which starts at the upper surface of the plug (11).

10. The apparatus of claim 6 wherein the plug (11) includes an upper surface and a lower surface and the scraper (12) is attached to the lower surface of the plug (11).

* * * * *